(12) United States Patent
Chang et al.

(10) Patent No.: US 7,049,400 B1
(45) Date of Patent: May 23, 2006

(54) MODIFIED FLUORESCENT PROTEINS FOR DETECTING PROTEASE ACTIVITY

(75) Inventors: Donald Choy Chang, Kowloon (HK); Qian Luo, Kowloon (HK)

(73) Assignee: The Hong Kong University of Science and Technology, Kowloon (HK)

( * ) Notice: Subject to any disclaimer, the term of this patent is extended or adjusted under 35 U.S.C. 154(b) by 0 days.

(21) Appl. No.: 09/551,380

(22) Filed: Apr. 18, 2000

(51) Int. Cl.
C07K 1/00 (2006.01)
C12N 9/00 (2006.01)
C12N 9/50 (2006.01)
C12N 1/20 (2006.01)
C12N 15/00 (2006.01)

(52) U.S. Cl. ............... 530/350; 435/183; 435/212; 435/219; 435/252.3; 435/320.1

(58) Field of Classification Search ............ 435/183, 435/219, 212, 252.3, 320.1; 530/350
See application file for complete search history.

(56) References Cited

U.S. PATENT DOCUMENTS

| | | | |
|---|---|---|---|
| 5,491,084 A | 2/1996 | Chalfie et al. | |
| 5,625,048 A | 4/1997 | Tsien et al. | |
| 5,777,079 A | 7/1998 | Tsien et al. | |
| 5,804,387 A | 9/1998 | Cormack et al. | |
| 5,981,200 A | 11/1999 | Tsien et al. | |

OTHER PUBLICATIONS

Branden et al.. Introduction to Protein Structure. New York and London: Garland Publishing, Inc. 1991, p. 271.*
Xu et al. Detection of programmed cell death using fluorescence energy transfer. Nucleic Acids Res. Apr. 15, 1998;26(8):2034-5.*
Cody et al. Biochemistry. Feb. 9, 1993;32(5):1212-8 (ABSTRACT).*
Thornberry et al, "A Combinatorial Approach Defines Specificites of Membes of the Caspase Family and Cranzyme B", *The Journal of Biological Chemistry*, vol. 272, No. 29, Issue of Jul. 18, 1997, pp. 17907-17911, USA.
"ApoAlert™ CPP32 Protease Assay Kits", CLONTECHniques, Jan., 1997, pp. 4-6, USA.
Geoffrey S. Braid et al, "Circular permutation and receptor insertion within green fluorescent proteins," *Proc. Natl. Acad. Sci. USA*, vol. 96, pp. 11241-11246, Sep., 1999, US.

Mats Ormo et al, "Crystal Structure of the *Qequorea victoria* Green Fluorescent Protein", *Science*, vol. 273, pp. 1392-1395, Sep. 6, 1996, US.
Fan Yang et al, "The molecular structure of green fluorescent protein", *Nature Biotechnology*, vol. 14, pp. 1246-1251, Oct. 14, 1996, US.
Rebekka M. Wachter et al, "Crystal Structure and Photodynamic Behavior of the Blue Emission Variant Y66H/Y145F of Green Fluorescent Protein", *Biochemistry*, vol. 36, pp. 9759-9765, 1997, American Chemical Society, US.
Daniel Yarbrough et al, "Refined crystal structure of DsRed, a red fluorescent protein from coral, at 2.0-A resolution", *Proc Natl Acad Sci USA*, vol. 98, pp. 462-467, Jan. 16, 2001, US.
Abstract of Article—*Engineering green fluorescent protein for improved brightness, longer wavelength and fluorescence resonance energy transfer*, R. Heim and T. Y. Tsien, Curr. Biol., Feb. 1996, 1 page.
Article—*Detection of programmed cell death using fluorescence energy transfer*, Xiang Xu, Amy L. V. Gerard, Betty C. B. Huang, David C. Anderson, Donald G. Payan, and Ying Luo, Nucleic Acids Research, vol. 26, No. 8, 1998, pp. 2034-2035.
Article—*Dual Labeling Using ECFP & EYFP in Standard Fluorescence Microscopy*, Brigitte Angres & Gisele Green, CLONTECH, Apr. 1999, 2 pages.

(Continued)

*Primary Examiner*—Tekchand Saidha
*Assistant Examiner*—Christian L. Fronda
(74) *Attorney, Agent, or Firm*—Dority & Manning, P.A.

(57) ABSTRACT

The present invention concerns fluorescent proteins modified such that said modified fluorescent protein incorporates a cleavage site for a protease, cleavage of said modified fluorescent protein at said cleavage site by said protease causing the alteration of at least one of the emission and excitation spectra of said modified fluorescent protein. In particular, the invention is concerned with using these modified fluorescent proteins as probes for detecting protease activity in living cells during the programmed cell death process (apoptosis).

Also provided are nucleic acid sequence encoding same, recombinant DNA constructs expressing same, cells transformed or transfected with same, methods for detecting protease activity, and methods of detecting agents which affect protease activity, and kits for same.

5 Claims, 7 Drawing Sheets

OTHER PUBLICATIONS

Article—*Understanding, improving and using green fluorescent proteins,* Andrew B. Cubitt, Roger Heim, Stephen R. Adams, Aileen E. Boyd, Larry A. Gross, and Roger Y. Tsien, Techniques, TIBS 20, Nov. 1995, pp. 448-455.

Product Information on ApoAlert™ Caspase Assay Kits from CLONTECH, 1 page.

Product Information on Living Colors™ pEBFP-N1 & -C1 Vectors from CLONTECH, 2 pages.

Query Result Browser on Green Fluorescent Protein from Protein Data Bank, 4 pages, www.rcsb.org.

Summary Information—Blue Variant Of Green Fluorescent Protein by R. M. Wachter, and S. J. Remington from Protein Data Bank, Deposition Date: Apr. 9, 1997, www.rcsb.org.

Summary Information—Green Fluorescent Protein (Gfp) From *Aequorea victoria,* Gln 80 Replaced With Arg by K. Brejc and T. Sixma from Protein Data Bank, Deposition Date: Jan. 8, 1997, www.rcsb.org.

Summary Information—Green Fluorescent Protein From *Aequorea victoria* by M. Ormo and S. J. Remington from Protein Data Bank, Deposition Date: Aug. 1, 1996, www.rcsb.org.

Summary Information—Green Fluorescent Protein From *Aequorea victoria,* Mutant by G. Palm, Z. Zdanov, and A. Wlodawer from Protein Data Bank, Deposition Date: Mar. 31, 1997, www.rcsb.org.

Summary Information—Green Fluorescent Protein Mutant F99S, M153T and V163A by R. Battistutta, A. Negro, and G. Zanotti from Protein Data Bank, Deposition Date: Feb. 9, 1999, www.rcsb.org.

Summary Information—Green Fluorescent Protein S65T At pH 4.6 by M. A. Elsliger, R. M. Wachter, K. Kallio, G. T. Hanson, and S. J. Remington from Protein Data Bank, Deposition Date: Aug. 21, 1999, www.rcsb.org.

Summary Information—Structure Of Yellow-Emission Variant Of Gfp by R. M. Wachter, M.-A. Elsliger, K. Kallio, G. T. Hanson, and S. J. Remington from Protein Data Bank, Deposition Date: Aug. 28, 1998, www.rcsb.org.

* cited by examiner

Locations of mutation sites in GFP 3D structure

SEQUENCE LISTING

```
<160> NUMBER OF SEQ ID NOS: 55

<210> SEQ ID NO 1
<211> LENGTH: 39
<212> TYPE: DNA
<213> ORGANISM: Artificial Sequence
<220> FEATURE:
<223> OTHER INFORMATION: PCR Primer
<221> NAME/KEY: CDS
<222> LOCATION: (3)..(38)
<223> OTHER INFORMATION:

<400> SEQUENCE: 1 ct cca att ggc gat gaa gtc gac ggc cct gtc ctt tta c      39
   Pro Ile Gly Asp Glu Val Asp Gly Pro Val Leu Leu
   1               5                  10

<210> SEQ ID NO 2
<211> LENGTH: 12
```

```
<212> TYPE: PRT
<213> ORGANISM: Artificial Sequence
<220> FEATURE:
<223> OTHER INFORMATION: PCR Primer

<400> SEQUENCE: 2

Pro Ile Gly Asp Glu Val Asp Gly Pro Val Leu Leu
1               5                   10

<210> SEQ ID NO 3
<211> LENGTH: 39
<212> TYPE: DNA
<213> ORGANISM: artificial sequence
<220> FEATURE:
<223> OTHER INFORMATION: PCR primer

<400> SEQUENCE: 3
gtaaaaggac agggccgtcg acttcatcgc caattggag                              39

<210> SEQ ID NO 4
<211> LENGTH: 4
<212> TYPE: PRT
<213> ORGANISM: Homo sapiens

<400> SEQUENCE: 4

Asp Glu Val Asp
1

<210> SEQ ID NO 5
<211> LENGTH: 720
<212> TYPE: DNA
<213> ORGANISM: artificial sequence
<220> FEATURE:
<223> OTHER INFORMATION: Possible cleavage site
<221> NAME/KEY: CDS
<222> LOCATION: (1)..(714)
<223> OTHER INFORMATION:

<400> SEQUENCE: 5 atg agt aaa gga gaa gaa ctt ttc act gga gtt gtc cca att ctt gtt       48
Met Ser Lys Gly Glu Glu Leu Phe Thr Gly Val Val Pro Ile Leu Val
1               5                   10                  15 gaa tta gat ggt gat gtt aat ggg cac aaa ttt tct gtc agt gga gag       96
Glu Leu Asp Gly Asp Val Asn Gly His Lys Phe Ser Val Ser Gly Glu
                20                  25                  30 ggt gaa ggt gat gca aca tac gga aaa ctt acc ctt aaa ttt att tgc      144
Gly Glu Gly Asp Ala Thr Tyr Gly Lys Leu Thr Leu Lys Phe Ile Cys
            35                  40                  45 act act gga aaa cta cct gtt cca tgg cca aca ctt gtc act act ttc      192
Thr Thr Gly Lys Leu Pro Val Pro Trp Pro Thr Leu Val Thr Thr Phe
        50                  55                  60 act tat ggt gtt caa tgc ttt tca aga tac cca gat cat atg aaa cag      240
Thr Tyr Gly Val Gln Cys Phe Ser Arg Tyr Pro Asp His Met Lys Gln
65                  70                  75                  80 cat gac ttt ttc aag agt gcc atg ccc gaa ggt tat gta cag gaa aga      288
His Asp Phe Phe Lys Ser Ala Met Pro Glu Gly Tyr Val Gln Glu Arg
                85                  90                  95 act ata ttt ttc aaa gat gac ggg aac tac aag aca cgt gct gaa gtc      336
Thr Ile Phe Phe Lys Asp Asp Gly Asn Tyr Lys Thr Arg Ala Glu Val
            100                 105                 110 aag ttt gaa ggt gat acc ctt gtt aat aga atc gag tta aaa ggt att      384
Lys Phe Glu Gly Asp Thr Leu Val Asn Arg Ile Glu Leu Lys Gly Ile
        115                 120                 125 gat ttt aaa gaa gat gga aac att ctt gga cac aaa ttg gaa tac aac      432
```

```
Asp Phe Lys Glu Asp Gly Asn Ile Leu Gly His Lys Leu Glu Tyr Asn
        130                 135                 140 tat aac tca cac aat gta tac atc atg gca gac aaa caa aag aat gga      480
Tyr Asn Ser His Asn Val Tyr Ile Met Ala Asp Lys Gln Lys Asn Gly
145                 150                 155                 160 atc aaa gtt aac ttc aaa att aga cac aac att gaa gat gga agc gtt      528
Ile Lys Val Asn Phe Lys Ile Arg His Asn Ile Glu Asp Gly Ser Val
                165                 170                 175 caa cta gca gac cat tat caa caa aat act cca att ggc gat ggc cct      576
Gln Leu Ala Asp His Tyr Gln Gln Asn Thr Pro Ile Gly Asp Gly Pro
            180                 185                 190 gtc ctt tta cca gac aac cat tac ctg tcc aca caa tct gcc ctt tcg      624
Val Leu Leu Pro Asp Asn His Tyr Leu Ser Thr Gln Ser Ala Leu Ser
        195                 200                 205 aaa gat ccc aac gaa aag aga gac cac atg gtc ctt ctt gag ttt gta      672
Lys Asp Pro Asn Glu Lys Arg Asp His Met Val Leu Leu Glu Phe Val
210                 215                 220 aca gct gct ggg att aca cat ggc atg gat gaa cta tac aaa taataa       720
Thr Ala Ala Gly Ile Thr His Gly Met Asp Glu Leu Tyr Lys
225                 230                 235

<210> SEQ ID NO 6
<211> LENGTH: 238
<212> TYPE: PRT
<213> ORGANISM: artificial sequence
<220> FEATURE:
<223> OTHER INFORMATION: Possible cleavage site

<400> SEQUENCE: 6

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220
```

```
Thr Ala Ala Gly Ile Thr His Gly Met Asp Glu Leu Tyr Lys
225                 230                 235
```

<210> SEQ ID NO 7
<211> LENGTH: 4
<212> TYPE: PRT
<213> ORGANISM: Homo sapiens

<400> SEQUENCE: 7

Tyr Val His Asp
1

<210> SEQ ID NO 8
<211> LENGTH: 4
<212> TYPE: PRT
<213> ORGANISM: artificial sequence
<220> FEATURE:
<223> OTHER INFORMATION: Caspase cleavage site

<400> SEQUENCE: 8

Asp Glu His Asp
1

<210> SEQ ID NO 9
<211> LENGTH: 4
<212> TYPE: PRT
<213> ORGANISM: artificial sequence
<220> FEATURE:
<223> OTHER INFORMATION: Possible cleavage site

<400> SEQUENCE: 9

Trp Glu His Asp
1

<210> SEQ ID NO 10
<211> LENGTH: 4
<212> TYPE: PRT
<213> ORGANISM: artificial sequence
<220> FEATURE:
<223> OTHER INFORMATION: Caspase cleavage site

<400> SEQUENCE: 10

Leu Glu His Asp
1

<210> SEQ ID NO 11
<211> LENGTH: 4
<212> TYPE: PRT
<213> ORGANISM: Homo sapiens

<400> SEQUENCE: 11

Val Glu Ile Asp
1

<210> SEQ ID NO 12
<211> LENGTH: 4
<212> TYPE: PRT
<213> ORGANISM: artificial sequence
<220> FEATURE:
<223> OTHER INFORMATION: Caspase cleavage site

<400> SEQUENCE: 12

Leu Glu Thr Asp
1

<210> SEQ ID NO 13

```
<211> LENGTH: 4
<212> TYPE: PRT
<213> ORGANISM: artificial sequence
<220> FEATURE:
<223> OTHER INFORMATION: Caspase cleavage site

<400> SEQUENCE: 13

Leu Glu His Asp
1

<210> SEQ ID NO 14
<211> LENGTH: 3
<212> TYPE: PRT
<213> ORGANISM: artificial sequence
<220> FEATURE:
<223> OTHER INFORMATION: Possible cleavage site

<400> SEQUENCE: 14

Glu Val Asp
1

<210> SEQ ID NO 15
<211> LENGTH: 3
<212> TYPE: PRT
<213> ORGANISM: artificial sequence
<220> FEATURE:
<223> OTHER INFORMATION: Possible cleavage site

<400> SEQUENCE: 15

Asp Glu Val
1

<210> SEQ ID NO 16
<211> LENGTH: 4
<212> TYPE: PRT
<213> ORGANISM: artificial sequence
<220> FEATURE:
<223> OTHER INFORMATION: Possible cleavage site

<400> SEQUENCE: 16

Asp Glu Asp Asp
1

<210> SEQ ID NO 17
<211> LENGTH: 5
<212> TYPE: PRT
<213> ORGANISM: artificial sequence
<220> FEATURE:
<223> OTHER INFORMATION: Possible cleavage site

<400> SEQUENCE: 17

Asp Glu Val Asp Gly
1               5

<210> SEQ ID NO 18
<211> LENGTH: 2
<212> TYPE: PRT
<213> ORGANISM: artificial sequence
<220> FEATURE:
<223> OTHER INFORMATION: Possible cleavage site

<400> SEQUENCE: 18

Glu Val
1

<210> SEQ ID NO 19
<211> LENGTH: 6
```

-continued

```
<212> TYPE: PRT
<213> ORGANISM: artificial sequence
<220> FEATURE:
<223> OTHER INFORMATION: Possible cleavage site

<400> SEQUENCE: 19

Asp Glu Val Asp Gly Thr
1               5

<210> SEQ ID NO 20
<211> LENGTH: 5
<212> TYPE: PRT
<213> ORGANISM: artificial sequence
<220> FEATURE:
<223> OTHER INFORMATION: Possible cleavage site

<400> SEQUENCE: 20

Glu Val Asp Gly Pro
1               5

<210> SEQ ID NO 21
<211> LENGTH: 5
<212> TYPE: PRT
<213> ORGANISM: artificial sequence
<220> FEATURE:
<223> OTHER INFORMATION: Possible cleavage site

<400> SEQUENCE: 21

Glu Val Asp Met Gly
1               5

<210> SEQ ID NO 22
<211> LENGTH: 5
<212> TYPE: PRT
<213> ORGANISM: artificial sequence
<220> FEATURE:
<223> OTHER INFORMATION: Possible cleavage site

<400> SEQUENCE: 22

Glu Val Asp Ser Gly
1               5

<210> SEQ ID NO 23
<211> LENGTH: 5
<212> TYPE: PRT
<213> ORGANISM: artificial sequence
<220> FEATURE:
<223> OTHER INFORMATION: Possible cleavage site

<400> SEQUENCE: 23

Glu Val Asp Arg Gly
1               5

<210> SEQ ID NO 24
<211> LENGTH: 5
<212> TYPE: PRT
<213> ORGANISM: artificial sequence
<220> FEATURE:
<223> OTHER INFORMATION: Possible cleavage site

<400> SEQUENCE: 24

Glu Val Asp Gly Gly
1               5

<210> SEQ ID NO 25
<211> LENGTH: 6
<212> TYPE: PRT
```

```
<213> ORGANISM: artificial sequence
<220> FEATURE:
<223> OTHER INFORMATION: Possible cleavage site

<400> SEQUENCE: 25

Ala Asp Glu Val Asp Ile
1               5

<210> SEQ ID NO 26
<211> LENGTH: 6
<212> TYPE: PRT
<213> ORGANISM: artificial sequence
<220> FEATURE:
<223> OTHER INFORMATION: Possible cleavage site

<400> SEQUENCE: 26

Trp Asp Glu Val Asp Val
1               5

<210> SEQ ID NO 27
<211> LENGTH: 6
<212> TYPE: PRT
<213> ORGANISM: artificial sequence
<220> FEATURE:
<223> OTHER INFORMATION: Possible cleavage site

<400> SEQUENCE: 27

Thr Asp Asp Val Asp Leu
1               5

<210> SEQ ID NO 28
<211> LENGTH: 6
<212> TYPE: PRT
<213> ORGANISM: artificial sequence
<220> FEATURE:
<223> OTHER INFORMATION: Possible cleavage site

<400> SEQUENCE: 28

Trp Asp Glu Val Asp Ala
1               5

<210> SEQ ID NO 29
<211> LENGTH: 6
<212> TYPE: PRT
<213> ORGANISM: artificial sequence
<220> FEATURE:
<223> OTHER INFORMATION: Possible cleavage site

<400> SEQUENCE: 29

Arg Asp Glu Val Asp Phe
1               5

<210> SEQ ID NO 30
<211> LENGTH: 5
<212> TYPE: PRT
<213> ORGANISM: artificial sequence
<220> FEATURE:
<223> OTHER INFORMATION: Possible cleavage site

<400> SEQUENCE: 30

Asp Glu Val Asp Gly
1               5

<210> SEQ ID NO 31
<211> LENGTH: 4
<212> TYPE: PRT
<213> ORGANISM: artificial sequence
```

```
<220> FEATURE:
<223> OTHER INFORMATION: Possible cleavage site

<400> SEQUENCE: 31

Glu Val Asp Gly
1

<210> SEQ ID NO 32
<211> LENGTH: 239
<212> TYPE: PRT
<213> ORGANISM: artificial sequence
<220> FEATURE:
<223> OTHER INFORMATION: EGFP - mammalian enhanced GFP

<400> SEQUENCE: 32

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 33
<211> LENGTH: 240
<212> TYPE: PRT
<213> ORGANISM: Artificial Sequence
<220> FEATURE:
<223> OTHER INFORMATION: D1 mutant of GFP(S65T)

<400> SEQUENCE: 33

Met Ser Lys Gly Glu Glu Leu Phe Thr Gly Val Val Pro Ile Leu Val
1               5                   10                  15

Glu Leu Asp Gly Asp Glu Val Asp Asn Gly His Lys Phe Ser Val Ser
            20                  25                  30
```

Gly Glu Gly Glu Gly Asp Ala Thr Tyr Gly Lys Leu Thr Leu Lys Phe
            35                  40                  45

Ile Cys Thr Thr Gly Lys Leu Pro Val Pro Trp Pro Thr Leu Val Thr
 50                  55                  60

Thr Phe Thr Tyr Gly Val Gln Cys Phe Ser Arg Tyr Pro Asp His Met
 65                  70                  75                  80

Lys Arg His Asp Phe Phe Lys Ser Ala Met Pro Glu Gly Tyr Val Gln
                 85                  90                  95

Glu Arg Thr Ile Phe Phe Lys Asp Asp Gly Asn Tyr Lys Thr Arg Ala
            100                 105                 110

Glu Val Lys Phe Glu Gly Asp Thr Leu Val Asn Arg Ile Glu Leu Lys
            115                 120                 125

Gly Ile Asp Phe Lys Glu Asp Gly Asn Ile Leu Gly His Lys Leu Glu
130                 135                 140

Tyr Asn Tyr Asn Ser His Asn Val Tyr Ile Met Ala Asp Lys Gln Lys
145                 150                 155                 160

Asn Gly Ile Lys Val Asn Phe Lys Ile Arg His Asn Ile Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
            195                 200                 205

Leu Ser Lys Asp Pro Asn Glu Lys Arg Asp His Met Val Leu Leu Glu
            210                 215                 220

Phe Val Thr Ala Ala Gly Ile Thr His Gly Met Asp Glu Leu Tyr Lys
225                 230                 235                 240

<210> SEQ ID NO 34
<211> LENGTH: 238
<212> TYPE: PRT
<213> ORGANISM: Artificial Sequence
<220> FEATURE:
<223> OTHER INFORMATION: D2 mutant of GFP(S65T)

<400> SEQUENCE: 34

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Asp Glu Val Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
 50                  55                  60

Thr Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

```
Ile Lys Val Asn Phe Lys Ile Arg His Asn Ile Glu Asp Gly Ser Val
            165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
            210                 215                 220

Thr Ala Ala Gly Ile Thr His Gly Met Asp Glu Leu Tyr Lys
225                 230                 235
```

<210> SEQ ID NO 35
<211> LENGTH: 240
<212> TYPE: PRT
<213> ORGANISM: Artificial Sequence
<220> FEATURE:
<223> OTHER INFORMATION: D3 mutant of GFP(S65T)

<400> SEQUENCE: 35

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Glu Asp Gly Asn Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Tyr Asn Ser His Asn Val Tyr Ile Met Ala Asp Lys Gln Lys
145                 150                 155                 160

Asn Gly Ile Lys Val Asn Phe Lys Ile Arg His Asn Ile Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205

Leu Ser Lys Asp Pro Asn Glu Lys Arg Asp His Met Val Leu Leu Glu
    210                 215                 220

Phe Val Thr Ala Ala Gly Ile Thr His Gly Met Asp Glu Leu Tyr Lys
225                 230                 235                 240
```

<210> SEQ ID NO 36
<211> LENGTH: 240
<212> TYPE: PRT
<213> ORGANISM: Artificial Sequence
<220> FEATURE:
<223> OTHER INFORMATION: D4 mutant of GFP(S65T)

<400> SEQUENCE: 36

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
 50                      55                  60

Thr Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Asp Glu Val Asp Gly Thr Leu Val Asn Arg Ile Glu Leu Lys
        115                 120                 125

Gly Ile Asp Phe Lys Glu Asp Gly Asn Ile Leu Gly His Lys Leu Glu
130                 135                 140

Tyr Asn Tyr Asn Ser His Asn Val Tyr Ile Met Ala Asp Lys Gln Lys
145                 150                 155                 160

Asn Gly Ile Lys Val Asn Phe Lys Ile Arg His Asn Ile Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205

Leu Ser Lys Asp Pro Asn Glu Lys Arg Asp His Met Val Leu Leu Glu
    210                 215                 220

Phe Val Thr Ala Ala Gly Ile Thr His Gly Met Asp Glu Leu Tyr Lys
225                 230                 235                 240

<210> SEQ ID NO 37
<211> LENGTH: 238
<212> TYPE: PRT
<213> ORGANISM: Artificial Sequence
<220> FEATURE:
<223> OTHER INFORMATION: D5 mutant of GFP(S65T)

<400> SEQUENCE: 37

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
 50                      55                  60

Thr Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125
```

-continued

```
Asp Glu Val Asp Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 38
<211> LENGTH: 237
<212> TYPE: PRT
<213> ORGANISM: Artificial Sequence
<220> FEATURE:
<223> OTHER INFORMATION: D6 mutant of GFP(S65T)

<400> SEQUENCE: 38

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Glu Val Asp Gly Asn Ile Leu Gly His Lys Leu Glu Tyr Asn Tyr
    130                 135                 140

Asn Ser His Asn Val Tyr Ile Met Ala Asp Lys Gln Lys Asn Gly Ile
145                 150                 155                 160

Lys Val Asn Phe Lys Ile Arg His Asn Ile Glu Asp Gly Ser Val Gln
                165                 170                 175

Leu Ala Asp His Tyr Gln Gln Asn Thr Pro Ile Gly Asp Gly Pro Val
            180                 185                 190

Leu Leu Pro Asp Asn His Tyr Leu Ser Thr Gln Ser Ala Leu Ser Lys
        195                 200                 205

Asp Pro Asn Glu Lys Arg Asp His Met Val Leu Leu Glu Phe Val Thr
    210                 215                 220

Ala Ala Gly Ile Thr His Gly Met Asp Glu Leu Tyr Lys
225                 230                 235
```

<210> SEQ ID NO 39

```
<211> LENGTH: 240
<212> TYPE: PRT
<213> ORGANISM: Artificial Sequence
<220> FEATURE:
<223> OTHER INFORMATION: D7 mutant of GFP(S65T)

<400> SEQUENCE: 39

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Asp Glu Val Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205

Leu Ser Lys Asp Pro Asn Glu Lys Arg Asp His Met Val Leu Leu Glu
    210                 215                 220

Phe Val Thr Ala Ala Gly Ile Thr His Gly Met Asp Glu Leu Tyr Lys
225                 230                 235                 240

<210> SEQ ID NO 40
<211> LENGTH: 242
<212> TYPE: PRT
<213> ORGANISM: Artificial Sequence
<220> FEATURE:
<223> OTHER INFORMATION: D8 mutant of GFP(S65T)

<400> SEQUENCE: 40

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
```

```
                85                  90                  95
Thr Ile Phe Phe Lys Asp Asp Gly Asn Tyr Lys Thr Arg Ala Glu Val
                100                 105                 110
Lys Phe Glu Gly Asp Glu Val Asp Gly Thr Leu Val Asn Arg Ile Glu
            115                 120                 125
Leu Lys Gly Ile Asp Phe Lys Glu Asp Gly Asn Ile Leu Gly His Lys
    130                 135                 140
Leu Glu Tyr Asn Tyr Asn Ser His Asn Val Tyr Ile Met Ala Asp Lys
145                 150                 155                 160
Gln Lys Asn Gly Ile Lys Val Asn Phe Lys Ile Arg His Asn Ile Glu
                165                 170                 175
Asp Gly Ser Val Gln Leu Ala Asp His Tyr Gln Gln Asn Thr Pro Ile
                180                 185                 190
Gly Asp Gly Pro Val Leu Leu Pro Asp Asn His Tyr Leu Ser Thr Gln
            195                 200                 205
Ser Ala Leu Ser Lys Asp Pro Asn Glu Lys Arg Asp His Met Val Leu
    210                 215                 220
Leu Glu Phe Val Thr Ala Ala Gly Ile Thr His Gly Met Asp Glu Leu
225                 230                 235                 240

Tyr Lys

<210> SEQ ID NO 41
<211> LENGTH: 241
<212> TYPE: PRT
<213> ORGANISM: Artificial Sequence
<220> FEATURE:
<223> OTHER INFORMATION: D9 mutant of GFP(S65T)

<400> SEQUENCE: 41

Met Ser Lys Gly Glu Glu Leu Phe Thr Gly Val Val Pro Ile Leu Val
1               5                   10                  15
Glu Leu Asp Gly Asp Val Asn Gly His Lys Phe Ser Val Ser Gly Glu
                20                  25                  30
Gly Glu Gly Asp Ala Thr Tyr Gly Lys Leu Thr Leu Lys Phe Ile Cys
            35                  40                  45
Thr Thr Gly Lys Leu Pro Val Pro Trp Pro Thr Leu Val Thr Thr Phe
    50                  55                  60
Thr Tyr Gly Val Gln Cys Phe Ser Arg Tyr Pro Asp His Met Lys Arg
65                  70                  75                  80
His Asp Phe Phe Lys Ser Ala Met Pro Glu Gly Tyr Val Gln Glu Arg
                85                  90                  95
Thr Ile Phe Phe Lys Asp Asp Gly Asn Tyr Lys Thr Arg Ala Glu Val
                100                 105                 110
Lys Phe Glu Gly Asp Thr Leu Val Asn Arg Ile Glu Leu Lys Gly Ile
            115                 120                 125
Asp Phe Lys Glu Asp Gly Asn Ile Leu Gly His Lys Leu Glu Tyr Asn
    130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Glu Val
            180                 185                 190
Asp Gly Pro Val Leu Leu Pro Asp Asn His Tyr Leu Ser Thr Gln Ser
        195                 200                 205
```

```
Ala Leu Ser Lys Asp Pro Asn Glu Lys Arg Asp His Met Val Leu Leu
    210                 215                 220

Glu Phe Val Thr Ala Ala Gly Ile Thr His Gly Met Asp Glu Leu Tyr
225                 230                 235                 240

Lys

<210> SEQ ID NO 42
<211> LENGTH: 242
<212> TYPE: PRT
<213> ORGANISM: Artificial Sequence
<220> FEATURE:
<223> OTHER INFORMATION: E2 mutant of GFP(S65T)

<400> SEQUENCE: 42

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Glu Val Asp Gly Pro Leu Val Asn Arg Ile Glu
        115                 120                 125

Leu Lys Gly Ile Asp Phe Lys Glu Asp Gly Asn Ile Leu Gly His Lys
    130                 135                 140

Leu Glu Tyr Asn Tyr Asn Ser His Asn Val Tyr Ile Met Ala Asp Lys
145                 150                 155                 160

Gln Lys Asn Gly Ile Lys Val Asn Phe Lys Ile Arg His Asn Ile Glu
                165                 170                 175

Asp Gly Ser Val Gln Leu Ala Asp His Tyr Gln Gln Asn Thr Pro Ile
            180                 185                 190

Gly Asp Gly Pro Val Leu Leu Pro Asp Asn His Tyr Leu Ser Thr Gln
        195                 200                 205

Ser Ala Leu Ser Lys Asp Pro Asn Glu Lys Arg Asp His Met Val Leu
    210                 215                 220

Leu Glu Phe Val Thr Ala Ala Gly Ile Thr His Gly Met Asp Glu Leu
225                 230                 235                 240

Tyr Lys

<210> SEQ ID NO 43
<211> LENGTH: 242
<212> TYPE: PRT
<213> ORGANISM: Artificial Sequence
<220> FEATURE:
<223> OTHER INFORMATION: E3-1 mutant of GFP(S65T)

<400> SEQUENCE: 43

Met Ser Lys Gly Glu Glu Leu Phe Thr Gly Val Val Pro Ile Leu Val
1               5                   10                  15
```

-continued

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
 50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
               100                 105                 110

Lys Phe Glu Gly Asp Thr Leu Val Asn Arg Ile Glu Leu Lys Gly Ile
           115                 120                 125

Asp Phe Lys Glu Asp Glu Val Asp Met Gly Asn Ile Leu Gly His Lys
       130                 135                 140

Leu Glu Tyr Asn Tyr Asn Ser His Asn Val Tyr Ile Met Ala Asp Lys
145                 150                 155                 160

Gln Lys Asn Gly Ile Lys Val Asn Phe Lys Ile Arg His Asn Ile Glu
                165                 170                 175

Asp Gly Ser Val Gln Leu Ala Asp His Tyr Gln Gln Asn Thr Pro Ile
            180                 185                 190

Gly Asp Gly Pro Val Leu Leu Pro Asp Asn His Tyr Leu Ser Thr Gln
        195                 200                 205

Ser Ala Leu Ser Lys Asp Pro Asn Glu Lys Arg Asp His Met Val Leu
    210                 215                 220

Leu Glu Phe Val Thr Ala Ala Gly Ile Thr His Gly Met Asp Glu Leu
225                 230                 235                 240

Tyr Lys

<210> SEQ ID NO 44
<211> LENGTH: 242
<212> TYPE: PRT
<213> ORGANISM: Artificial Sequence
<220> FEATURE:
<223> OTHER INFORMATION: E3-5 mutant of GFP(S65T)

<400> SEQUENCE: 44

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
 50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
               100                 105                 110

Lys Phe Glu Gly Asp Thr Leu Val Asn Arg Ile Glu Leu Lys Gly Ile
           115                 120                 125

Asp Phe Lys Glu Asp Glu Val Asp Ser Gly Asn Ile Leu Gly His Lys

```
            130                 135                 140
Leu Glu Tyr Asn Tyr Asn Ser His Asn Val Tyr Ile Met Ala Asp Lys
145                 150                 155                 160

Gln Lys Asn Gly Ile Lys Val Asn Phe Lys Ile Arg His Asn Ile Glu
                165                 170                 175

Asp Gly Ser Val Gln Leu Ala Asp His Tyr Gln Gln Asn Thr Pro Ile
            180                 185                 190

Gly Asp Gly Pro Val Leu Leu Pro Asp Asn His Tyr Leu Ser Thr Gln
        195                 200                 205

Ser Ala Leu Ser Lys Asp Pro Asn Glu Lys Arg Asp His Met Val Leu
    210                 215                 220

Leu Glu Phe Val Thr Ala Ala Gly Ile Thr His Gly Met Asp Glu Leu
225                 230                 235                 240

Tyr Lys

<210> SEQ ID NO 45
<211> LENGTH: 242
<212> TYPE: PRT
<213> ORGANISM: Artificial Sequence
<220> FEATURE:
<223> OTHER INFORMATION: E3-9 mutant of GFP(S65T)

<400> SEQUENCE: 45

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Glu Val Asp Arg Gly Asn Ile Leu Gly His Lys
    130                 135                 140

Leu Glu Tyr Asn Tyr Asn Ser His Asn Val Tyr Ile Met Ala Asp Lys
145                 150                 155                 160

Gln Lys Asn Gly Ile Lys Val Asn Phe Lys Ile Arg His Asn Ile Glu
                165                 170                 175

Asp Gly Ser Val Gln Leu Ala Asp His Tyr Gln Gln Asn Thr Pro Ile
            180                 185                 190

Gly Asp Gly Pro Val Leu Leu Pro Asp Asn His Tyr Leu Ser Thr Gln
        195                 200                 205

Ser Ala Leu Ser Lys Asp Pro Asn Glu Lys Arg Asp His Met Val Leu
    210                 215                 220

Leu Glu Phe Val Thr Ala Ala Gly Ile Thr His Gly Met Asp Glu Leu
225                 230                 235                 240

Tyr Lys
```

<210> SEQ ID NO 46
<211> LENGTH: 242
<212> TYPE: PRT
<213> ORGANISM: Artificial Sequence
<220> FEATURE:
<223> OTHER INFORMATION: E3-12 mutant of GFP(S65T)

<400> SEQUENCE: 46

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Glu Val Asp Gly Gly Asn Ile Leu Gly His Lys
    130                 135                 140

Leu Glu Tyr Asn Tyr Asn Ser His Asn Val Tyr Ile Met Ala Asp Lys
145                 150                 155                 160

Gln Lys Asn Gly Ile Lys Val Asn Phe Lys Ile Arg His Asn Ile Glu
                165                 170                 175

Asp Gly Ser Val Gln Leu Ala Asp His Tyr Gln Gln Asn Thr Pro Ile
            180                 185                 190

Gly Asp Gly Pro Val Leu Leu Pro Asp Asn His Tyr Leu Ser Thr Gln
        195                 200                 205

Ser Ala Leu Ser Lys Asp Pro Asn Glu Lys Arg Asp His Met Val Leu
    210                 215                 220

Leu Glu Phe Val Thr Ala Ala Gly Ile Thr His Gly Met Asp Glu Leu
225                 230                 235                 240

Tyr Lys
```

<210> SEQ ID NO 47
<211> LENGTH: 243
<212> TYPE: PRT
<213> ORGANISM: Artificial Sequence
<220> FEATURE:
<223> OTHER INFORMATION: E4-a mutant of GFP(S65T)

<400> SEQUENCE: 47

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60
```

```
Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Ala Asp Glu Val Asp Ile Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys
```

<210> SEQ ID NO 48
<211> LENGTH: 243
<212> TYPE: PRT
<213> ORGANISM: Artificial Sequence
<220> FEATURE:
<223> OTHER INFORMATION: E4-g mutant of GFP(S65T)

<400> SEQUENCE: 48

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
```

-continued

```
                    180                 185                 190
Trp Asp Glu Val Asp Val Leu Leu Pro Asp Asn His Tyr Leu Ser Thr
            195                 200                 205

Gln Ser Ala Leu Ser Lys Asp Pro Asn Glu Lys Arg Asp His Met Val
        210                 215                 220

Leu Leu Glu Phe Val Thr Ala Ala Gly Ile Thr His Gly Met Asp Glu
225                 230                 235                 240

Leu Tyr Lys

<210> SEQ ID NO 49
<211> LENGTH: 243
<212> TYPE: PRT
<213> ORGANISM: Artificial Sequence
<220> FEATURE:
<223> OTHER INFORMATION: E4-j mutant of GFP(S65T)

<400> SEQUENCE: 49

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Thr Asp Val Asp Leu Leu Pro Asp Asn His Tyr Leu Ser Thr
        195                 200                 205

Gln Ser Ala Leu Ser Lys Asp Pro Asn Glu Lys Arg Asp His Met Val
    210                 215                 220

Leu Leu Glu Phe Val Thr Ala Ala Gly Ile Thr His Gly Met Asp Glu
225                 230                 235                 240

Leu Tyr Lys

<210> SEQ ID NO 50
<211> LENGTH: 243
<212> TYPE: PRT
<213> ORGANISM: Artificial Sequence
<220> FEATURE:
<223> OTHER INFORMATION: E4-o mutant of GFP(S65T)

<400> SEQUENCE: 50
```

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Trp Asp Glu Val Asp Ala Leu Leu Pro Asp Asn His Tyr Leu Ser Thr
        195                 200                 205

Gln Ser Ala Leu Ser Lys Asp Pro Asn Glu Lys Arg Asp His Met Val
210                 215                 220

Leu Leu Glu Phe Val Thr Ala Ala Gly Ile Thr His Gly Met Asp Glu
225                 230                 235                 240

Leu Tyr Lys

<210> SEQ ID NO 51
<211> LENGTH: 243
<212> TYPE: PRT
<213> ORGANISM: Artificial Sequence
<220> FEATURE:
<223> OTHER INFORMATION: E4-p mutant of GFP(S65T)

<400> SEQUENCE: 51

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110
```

-continued

```
Lys Phe Glu Gly Asp Thr Leu Val Asn Arg Ile Glu Leu Lys Gly Ile
            115                 120                 125
Asp Phe Lys Glu Asp Gly Asn Ile Leu Gly His Lys Leu Glu Tyr Asn
        130                 135                 140
Tyr Asn Ser His Asn Val Tyr Ile Met Ala Asp Lys Gln Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Arg Asp Glu Val Asp Phe Leu Leu Pro Asp Asn His Tyr Leu Ser Thr
        195                 200                 205
Gln Ser Ala Leu Ser Lys Asp Pro Asn Glu Lys Arg Asp His Met Val
210                 215                 220
Leu Leu Glu Phe Val Thr Ala Ala Gly Ile Thr His Gly Met Asp Glu
225                 230                 235                 240
Leu Tyr Lys
```

<210> SEQ ID NO 52
<211> LENGTH: 239
<212> TYPE: PRT
<213> ORGANISM: Artificial Sequence
<220> FEATURE:
<223> OTHER INFORMATION: Beta6 mutant of EGFP

<400> SEQUENCE: 52

```
Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
            20                  25                  30
Glu Gly Glu Gly Asp Ala Thr Tyr Gly Lys Leu Thr Leu Lys Phe Ile
        35                  40                  45
Cys Thr Thr Gly Lys Leu Pro Val Pro Trp Pro Thr Leu Val Thr Thr
    50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
Ile Asp Glu Val Asp Gly Gly Asn Ile Leu Gly His Lys Leu Glu Tyr
    130                 135                 140
Asn Tyr Asn Ser His Asn Val Tyr Ile Met Ala Asp Lys Gln Lys Asn
145                 150                 155                 160
Gly Ile Lys Val Asn Phe Lys Ile Arg His Asn Ile Glu Asp Gly Ser
                165                 170                 175
Val Gln Leu Ala Asp His Tyr Gln Gln Asn Thr Pro Ile Gly Asp Gly
            180                 185                 190
Pro Val Leu Leu Pro Asp Asn His Tyr Leu Ser Thr Gln Ser Ala Leu
        195                 200                 205
Ser Lys Asp Pro Asn Glu Lys Arg Asp His Met Val Leu Leu Glu Phe
    210                 215                 220
Val Thr Ala Ala Gly Ile Thr Leu Gly Met Asp Glu Leu Tyr Lys
```

-continued

<210> SEQ ID NO 53
<211> LENGTH: 239
<212> TYPE: PRT
<213> ORGANISM: Artificial Sequence
<220> FEATURE:
<223> OTHER INFORMATION: Beta9 mutant of EGFP

<400> SEQUENCE: 53

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Glu
            180                 185                 190

Val Asp Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 54
<211> LENGTH: 239
<212> TYPE: PRT
<213> ORGANISM: Artificial Sequence
<220> FEATURE:
<223> OTHER INFORMATION: Beta10 mutant of EGFP

<400> SEQUENCE: 54

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60
```

```
Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Glu Val Asp Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 55
<211> LENGTH: 242
<212> TYPE: PRT
<213> ORGANISM: Artificial Sequence
<220> FEATURE:
<223> OTHER INFORMATION: MD9 mutant of EGFP

<400> SEQUENCE: 55

Met Val Ser Lys Gly Glu Glu Leu Phe Thr Gly Val Val Pro Ile Leu
 1               5                  10                  15

Val Glu Leu Asp Gly Asp Val Asn Gly His Lys Phe Ser Val Ser Gly
                 20                  25                  30

Glu Gly Glu Gly Asp Ala Thr Tyr Gly Lys Leu Thr Leu Lys Phe Ile
             35                  40                  45

Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Glu
            180                 185                 190
```

-continued

```
Val Asp Gly Pro Val Leu Leu Pro Asp Asn His Tyr Leu Ser Thr Gln
        195                 200                 205

Ser Ala Leu Ser Lys Asp Pro Asn Glu Lys Arg Asp His Met Val Leu
    210                 215                 220

Leu Glu Phe Val Thr Ala Ala Gly Ile Thr Leu Gly Met Asp Glu Leu
225                 230                 235                 240

Tyr Lys
```

MODIFIED FLUORESCENT PROTEINS FOR DETECTING PROTEASE ACTIVITY

FIELD OF THE INVENTION

The present invention concerns modified fluorescent proteins, particularly modified green fluorescent proteins (GFPs), having a protease cleavage site whose cleavage causes the alteration of one or both of the emission and excitation spectra of the fluorescent protein. It also concerns methods for detecting protease activity and agents which affect same.

BACKGROUND OF THE INVENTION

Fluorescent proteins, particularly green fluorescent proteins, and their uses are well known in the art. U.S. Pat. No. 5,491,084 discloses various uses of a green fluorescent protein, together with host cells having gene constructs encoding a GFP, and methods for selecting cells expressing a protein-of interest. U.S. Pat. Nos. 5,625,048 and 5,777,079 disclose modified GFPs having emission and excitation spectra different to those of wild-type GFPs. U.S. Pat. No. 5,804,387 discloses GFP mutants having modified excitation and emission spectra.

Determining in vivo protease activity is extremely desirable since proteases can have a significant effect upon cellular events. For example, the early stage of apoptosis (programmed cell death) is signified by protease (caspase) activity and so an assay for appropriate protease activity can be an assay for apoptosis. Apoptosis is an induced cell suicidal process that allows the biological organism to destroy damaged or unwanted cells in an orderly way (Kerr, J. F. R. et al., 1972, Br. J. Cancer, 26: 239–257), and because of this it is a very important cellular process. It plays a vital role in maintaining the normal physiological function in a variety of ways. For example, the process of apoptosis is used in the thymus to eliminate self-reactive T cells to avoid auto-immunity (Thompson, C. B., 1995, Science, 267: 1456). Furthermore, when DNA is damaged in a cell and cannot be repaired, the cell will enter apoptosis to avoid the formation of abnormalities in the tissue. Thus, failure of programmed cell death can cause cancer. On the other hand, excessive apoptosis can also cause great damage to the body; it is linked to many neural degenerative diseases such as Huntington disease and Alzheimer's disease.

In the last few years, a large number of studies have been conducted aiming to understand the process of apoptosis on a molecular basis. The signalling pathways that direct the programmed cell death process turns out to be very complicated (Ashkenazi, A. and Dixit, V. M., 1998, Science, 281: 1305–1308; Thornberry, N. A. and Lazebnik, Y., 1998, Science, 281: 1312–1316; Evan, G. and Littlewood, T., 1998, Science, 281: 1322–1326; Adams, J. M. and Cory, S., 1998, Science, 281: 1317–1322). There are many external signals that can trigger the initiation of apoptosis, including UV-irradiation, activation of the "death domain" via the TNF (tumour necrosis factor) receptor or CD95, treatment with hormones (e.g. glucocorticoid) or chemotherapy drugs (e.g. camptothecin) (Ashkenazi, A. and Dixit, V. M., 1998, supra; Nagata, S., 1997, Cell, 88: 355–365; Martin, S. J. and Cotter, T. G., 1991, Int. Radiat. Biol., 59: 1001–1016). As for the internal signals, it is known that apoptosis is the outcome of a programmed cascade of intracellular events, which are centred on the activation of a class of cysteine proteases called "caspases" (Thornberry, N. A. and Lazebnik, Y., 1998, supra). At present, the detailed molecular mechanisms by which apoptosis is regulated by the various internal and external signals are still not well understood.

The process of apoptosis can be detected at different stages. For example, some apoptosis assays are based on events that occur rather late in apoptosis, such as morphological changes of the cell, nuclear breakdown, and chromosomal fragmentation. Some assays can detect relatively early events such as the turn-over of certain phospholipids in the membrane (Martin, S. J. et al., 1995, J. Exp. Med., 182: 1545–1555). Alternatively, one can assay the activation of caspase-3 based on the fact that substrates of caspase-3 have a specific sensing and cleavage sequence (Nicholson, D. W., 1996, Nature Biotechnol., 14: 297–301). By linking a peptide encoding this substrate sequence to a fluorescent dye, one can detect a shift of the fluorescent properties of the dye when the peptide is cleaved by the activated caspase (CLONTECHniques, 1997, 12(1): 4–6). The activity of caspase-8 can be similarly assayed (www.clontech.com, ApoAlert Caspase Assay Kits). Since these methods utilize an optical detection, they are simple and quick. These methods do, however, have certain limitations. For example, the probes cannot penetrate the cell membrane, thus it is difficult to load the probes inside the cell. The assays are therefore done using crude cell lysates, i.e. not with whole (living) cells and not in vivo. Furthermore, the fluorescent change resulting from caspase cleavage involves mainly a shift of the emission spectrum (from blue to yellow-green) rather than an easier to assay total destruction of the fluorescence. In addition, its sensitivity is limited.

BRIEF SUMMARY OF THE INVENTION

The present inventors have succeeded in providing a simple, accurate, easy-to-assay system for determining protease activity, particularly caspase activity, which works both in vivo and in vitro.

According to the present invention there is provided a fluorescent protein modified such that said modified fluorescent protein incorporates a cleavage site for a protease, cleavage of said modified fluorescent protein at said cleavage site by said protease causing the alteration of at least one of the emission and excitation spectra of said modified fluorescent protein. In particular, the invention is concerned with modified green fluorescent proteins.

Also provided are nucleic acid sequence encoding same, recombinant DNA constructs expressing same, cells transformed or transfected with same, methods for detecting protease activity, and methods of detecting agents which affect protease activity, and kits for same.

Although particularly useful in detecting caspase activity, the invention also extends to modified fluorescent proteins cleavable by other proteases to alter at least one of its emission and excitation spectra.

DETAILED DESCRIPTION OF THE INVENTION

Figure 1:
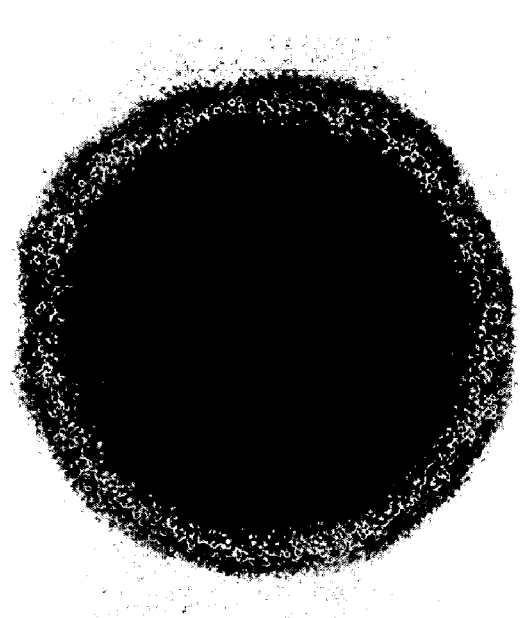
FIG. 1 shows bacterial colony expression of the wild-type GFP (top) and the GFP-DEVD mutant (bottom) on LB agar plate.
Figure 1:
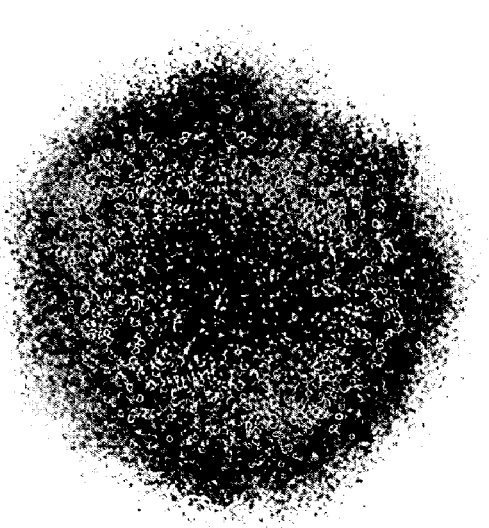

The gene for GFP was originally isolated from the jellyfish *Aequoea Victoria* (Prasher, D. C. et al., 1992, Gene, 111: 229–233). Its gene product contains a spontaneously formed chromophore generated through an oxygen-dependent cyclization reaction involving three amino acids (residue 65–67) (Cubitt, A. B. et al., 1995, TIBS, 20: 448–455). This gene can be expressed in cells of many different biological systems to produce an endogenous fluorescent protein without the requirement of adding exogenous substrates or coenzymes (Cubitt, A. B. et al., 1995, supra; Chalfie, M. et al., 1994, Science, 263: 802–805). In the last several years, GFP has been used widely in cell and molecular biology. For example, GFP has been used as reporters of gene expression, tracers of cell lineage, and fusion tags for monitoring protein localization within living cells (Cubitt, A. B. et al., 1995, supra; Gerdes, H. H. and Kaether, C., 1994, FEBS Lett., 384: 44–47).

The experiments below detail the production of modified green fluorescent proteins having caspase-specific recognition sites, the modified green fluorescent proteins being cleaved by the caspase enzymes only at the caspase-specific recognition sites. The efficacy of these recognition sites in enabling cleavage which affects fluorescence in the presence of a caspase specific against them varies between the differently modified GFPs, and the best modified protein produced so far is D9 (below) which is cleavable by a caspase and displays the greatest change in fluorescence (i.e. change in emission and/or excitation spectra) upon cleavage. Other useful modified proteins which can be cleaved by a caspase resulting in a change in fluorescence are D4, D7 and D8. The experiments show cleavage by caspase-3. Recognition sequences for other proteases are well known (see for example Table 3), and so can be readily incorporated into a modified fluorescent protein, for example in a modified GFP at the sites used to make D9, D4, D7 or D8 (see below). The sequences of SEQ ID NOs: 8–10, 12 and 13 contain optimal sequences for caspase recognition and cleavage and are artificial sequences defined by a positional screening of a tetrapeptide library for their caspase substrate specificity (Thornberry, M. A. et al., 1997, J. of Bio. Chem., 272: 17907–17911). More generally, modifications to incorporate a cleavage site can be at the loop structures of fluorescent proteins such as GFPs joining β-sheets, for example GFP β-sheets numbers 9 and 10, 5 and 6, or 8 and 9, the β-sheets being exposed on the exterior of the fluorescent protein.

As well as providing modified fluorescent proteins, nucleic acid sequences encoding same are also provided and are readily derived from the amino acid sequences of the proteins. The nucleic acid sequences encoding the proteins are used to produce recombinant DNA constructs additionally comprising a regulatory element operatively linked to the nucleic acid sequence, the regulatory element directing (i.e. being sufficient to drive) expression of the protein coded for. Regulatory elements are widely known and include those which cause constitutive expression, and those which are triggered by specif events or stimuli. Also provided are cells transformed or transfected with such recombinant DNA constructs. Such cells are particularly useful since they provide for the in vivo assay of protease levels. Techniques useful in achieving this are well known in the art and are described by e.g. Sambrook, J., Frisch, E. F., and Maniatis, T., "Molecular Cloning. A Laboratory Manual", Cold Spring Harbor Laboratory, Cold Spring Harbor Press, New York, 1989; "PCR (Volume 1): A practical approach" Eds. M. J. McPherson, P. Quirke and G. R. Taylor. Oxford University Press, 1991; "General Techniques of Cell Culture", Harris, M. A. and Rae, I. F., 1997, Cambridge University Press, ISBN 0521 573645; Huynh and Davies, 1985, "DNA Cloning Vol I—A Practical Approach", IRL Press, Oxford, Ed. D. M. Glover.

The proteins of the invention are useful in a number of applications, particularly assays for determining levels of protease activity in a sample, in determining changes in protease activity in a sample and in determining whether specific compounds or other substances affect protease activity in a sample. Specific samples include living cells—sample cells having a protease activity to be determined and control cells having a known protease activity which are used in assays to determine protease activity in the sample cell with reference to the known protease activity in the control cell. In detecting changes in protease activity, only the sample cell is needed with observations of fluorescence at different timepoints allowing changes in protease activity to be determined. Using at least three timepoints allows the rate of change to be determined, and can be standardised by reference to changes in a control sample having a known protease activity. Control samples can simply have no protease activity. Samples can also of course be other than living cells, for example crude cell lysates.

Substrates of a specific caspase often share a consensus recognition and cleavage amino acid sequence (Nicholson, D. W., 1996, supra). For example, the recognition sequence for caspase-3 is SEQ ID NO: 4. Using genetic engineering techniques, a molecular probe to assay the caspase-3 activity was produced by inserting the gene encoding its recognition/cleavage sequence into the gene encoding GFP. When this mutated GFP is expressed in a cell, its gene product (i.e. a modified GFP protein containing the specific caspase-3 recognition/cleavage sequence) is cleaved by the caspase upon its activation. The caspase-3 site can readily be replaced by the recognition and cleavage site of another caspase such as caspase-8 or caspase-9 (see Table 3). It can also be replaced by the cleavage site of any other protease and so can allow for the assaying of the activity of any chosen protease. The term "cleavage site" is used herein to refer to both the recognition and cleavage sites of a protease.

As discussed above, caspase activity in a cell, particularly caspase-3 activity, correlates with the start of programmed cell death (apoptosis). This means that a particularly useful assay is that of caspase-3 activity in order to determine the onset of apoptosis, its progress, and also to identify whether given compounds, substances or compositions (herein "compounds") have an effect upon apoptosis. For example, this can allow the detection of agents which trigger the start of apoptosis or hinder it, or in the case of patients such as certain cancer patients having cancer cells which are unable to undergo apoptosis, it allows the detection of agents which can re-enable apoptosis in such cells. Similarly this can also allow the identification and testing of first compounds which modify the apoptosis-inducing ability of second compounds, for example the second compound could be an environmental poison and the first compound an inhibitor of that poison.

In particular, in vivo assays can be performed using a continual analysis of excitation/emission spectra of a sample to determine the exact point at which apoptosis begins, as determined by caspase-3 activity. This resolution in the time domain has not previously been possible using e.g. cell lysates since they require time-consuming steps in order to perform an assay starting with complete sample cells/ In addition such assays are much less resource-intensive since a single preparation of a cell or cells can be used at many time-points instead of just one. Regarding the analysis of the excitation and/or emission spectra, this can be done with entire spectra or by "windowing" i.e. by analysing only a specific frequency range or ranges within the emission and/or excitation spectra. For example, this can be done using filters for incident and emitted light, which isolate a specific range of wavelengths. Similarly, when cleavage results in an overall destruction of fluorescence, the fluorescence intensity of a sample may be assayed, without reference to specific frequencies. Reference herein to determining, comparing and correlating emission and/or excitation spectra therefore includes determining, comparing and correlating the emission and/or excitation spectra at specific frequencies or ranges of frequencies, as well as overall fluorescence intenesity.

The invention also extends to fluorescent proteins other than GFP, and in particular concerns BFP (blue fluorescent protein), CFP (cyan fluorescent protein), YFP (yellow fluorescent protein)—fluorescent proteins available from e.g. Clontech and PharMingen—and DsRed (a red fluorescent protein isolated from *Discosoma striata*—Matz, M. V. et al., Nature Biotechnol., 17: 969–973) modified such that they incorporate a cleavage site for a protease, such that cleavage of said modified fluorescent protein at said cleavage site by said protease causes the alteration of at least one of the emission and excitation spectra of said modified fluorescent protein. The loop structures of the fluorescent protein which join β-sheets and which are exposed on the exterior of the fluorescent protein are particularly good sites for modification to incorporate a cleavage site.

EXAMPLES

In the design of our molecular probe, we place the caspase recognition sequence into specific intra-molecular locations of the GFP such that (i) the insertion does not destroy the fluorescent properties of the GFP, and (ii) the substrate is well accessible to the protease. Since GFP is known to have a very "tight" structure, the possible insertion locations that can satisfy both of these conditions are limited. X-ray diffraction studies have indicated that the crystal structure of GFP is an 11-stranded β-barrel with a coaxial α-helix, with the chromophore forming from the central helix (Ormo, M. et al., 1996, Science, 273: 1392–1395; Yang, F. et al., 1996, Nature Biotechnol., 14: 1246–1251). The major candidates for insertion are the loops between the various adjacent β-sheets, in particular the loops between the β-sheets numbers 5 and 6 (D4 and D8), 8 and 9 (D7), and 9 and 10 (D9). Also, in order to avoid a significant change of protein folding, the mutation must have minimal disturbance on the charge properties of the protein at the insertion site.

With this new molecular probe, activation of apoptosis can be assayed easily in living cells. The typical procedure of using this method to detect apoptosis is:

1. The plasmid DNA containing a modified GFP gene is introduced into host cells by standard gene transfer methods, such as electroporation, calcium phosphate or lipofectin.
2. When the transferred gene is expressed, the presence of the gene product (i.e. the modified GFP protein) can be detected by its green fluorescence using an optical device, such as a fluorescence microscope, a fluorescent activated cell sorter (FACS), or a fluorometer.
3. The transfected cells are then ready for induction to enter apoptosis. Depending on the purpose of the experiment, apoptosis can be induced by a number of means, such as treating the cells by TNF, UV or glucocorticoid.
4. When the caspase-3 is activated during apoptosis, it cleaves the modified GFP molecule at the substrate insertion site. This cleavage results in a dramatic change of the fluorescent properties of the GFP, which can be easily detected using an optical device (above) such as a fluorescence microscope. In this way, one can easily assay whether or not a particular cell or a population of cells are undergoing programmed cell death.

Furthermore, using a stable transfection technique, the gene encoding the molecular probe can be permanently inserted into the chromosomes of the target cells. In such a way, stable cell lines can be generated that can automatically generate the mutated GFP probe. Such cell lines can then be used of in vivo assay of apoptosis. These cell lines are particularly useful for rapid screening of drugs or for toxicity testing.

Example 1

Materials and Methods

Cell Lines and Culture Media

*Escherichia coli* BL21-DE-3 (Invitrogen, CA, USA) and DH5α (Life Technologies Inc., USA) were grown either in liquid LB (Luria-Bertani) medium or on a solid LB agar plate. The Oxoid tryptone and yeast extract for preparing LB culture media were obtained from Unipath Ltd. (Basingstoke, Hampshire, England). The select agar for making LB agar plates was obtained from Life Technologies Inc. (Paisley, Scotland). The HeLa cells were grown in MEM (Minimum Essential Medium) supplemented with 10% FBS (Fetal Bovine Serum), 100 U/ml penicillin, 100 U/ml streptomycin (Life Technologies Inc., Grand Island, N.Y., USA) and 0.37% NaHCO$_3$ (BDH Laboratory Supplies, Poole, England).

Modified Site-Directed Mutagenesis

The essential procedures of site-directed mutagenesis are described in the following: Two complementary oligonucleotide primers (see for example SEQ ID NOs: 1 and 3) containing DNA sequence encoding amino acids of SEQ ID NO: 4 in the middle of the primer and 13–17 bp of GFP gene specific sequence on both sides of the SEQ ID NO: 4 sequence were synthesized and cleaned up using QIAquick Nucleotide Removal Kit obtained from QIAGEN (Germany). A double-stranded plasmid containing the gene encoding GFP(S65T) (SEQ ID NO: 5; Heim, R. et al., 1995, Nature, 373: 664–664) was used as a template in the mutagenesis reaction, which comprised the following steps:

(1) The template was first denatured at 96° C. for 1–2 minutes
(2) The mutagenic primers were allowed to bind to the single-stranded DNA template at an annealing temperature
(3) Using a high fidelity Pwo DNA polymerase obtained from Boehringer Mannheim (Mannheim, Germany), the primers were extended at 68° C. for 10 minutes to synthesize a nicked circular plasmid A total of 18–20 cycles of the reaction were performed. After the amplification reaction, the nonmutated parental DNA of GFP(S65T) was digested by DpnI endonuclease that specifically digests methylated and hemimethylated DNA produced by bacteria. The nonmethylated nicked plasmids, newly generated by primer extension, were transferred into the bacteria host *E. coli* BL21-DE-3 cells, which ligate the mutated plasmids into circular plasmids and amplify them. These mutated plasmid DNA were isolated from the bacteria using High Pure Plasmid Isolation Kit obtained from Boehringer Mannheim and subjected to further analysis.

23 GFP mutants were generated using this modified site-directed mutagenesis method and are detailed in Tables 1 and 2. 19 of the GFP mutants were constructed using the GFP(S65T) gene (below; Table 1), whilst 4 were generated by mutating the EGFP gene (Table 2) which is optimised for expression in a mammalian host. The experimental condition for each primer extension reaction was adjusted according to the type of the mutation, such as single amino acids insertion or multiple amino acids insertion or replacement.

The following example shows a detailed procedure for constructing one of the GFP mutants, D9. Other mutants (i.e. modified GFPs) were similarly generated but resulted in different modifications.

Generation of D9 Mutant

In this experiment, three amino acids (EVD) were inserted into GFP(S65T) at the position between $D_{190}$–$G_{191}$ (see Table 1) in the following steps:

1). Two complementary mutagenic primers (KL35 and KL36) were synthesized by Life Technologies (Pacific) Ltd., and further purified using QIAquick Nucleotide Purification Kit (from QIAGEN) according to the manufacturer's protocol. The DNA and amino acids sequences for the 5' primer (KL35) are SEQ ID NOs: 1 and 2 respectively. KL36 is SEQ ID NO: 3.

2). Prepare the sample and control reactions on ice as indicated below:

| Components | Sample | Negative Control |
|---|---|---|
| 10× reaction buffer | 5 µl | 5 µl |
| 10 mM dNTPs | 1 µl | 1 µl |
| 5' primer (KL35) (10 pmol/µl) | 3 µl | 3 µl |
| 3' primer (KL36) (10 pmol/µl) | 3 µl | 3 µl |
| dsDNA template (10 ng/µl) | 5 µl | 0 |
| Double-distilled water (ddH$_2$O) | 33 µl | 38 µl |

Mix all the components and add 0.5 µl of Pwo DNA polymerase (5 U/µl) (from Boehringer Mannheim) into each tube. Put the reaction tubes into the PCR machine when the temperature of the PCR machine is higher than 85° C.

3). Run the reaction in the following temperature cycling:

| Steps | Function | Temperature and Time |
|---|---|---|
| 1 | pre-denaturation | at 96° C. for 2 minutes |
| 2 | denaturation | at 96° C. for 1 minute |
| 3 | annealing | at 55° C. for 1 minute |
| 4 | extension | at 68° C. for 9 minutes |
| 5 | repeat steps 2–4 for 17 more cycles | |
| 6 | final extension | at 72° C. for 15 minutes |
| 7 | cooling | at 4° C. for 5 minutes |
| 8 | end | |

4). Purify the PCR product from primers, nucleotides, polymerase and salts using QIAquick PCR Purification Kit (from QIAGEN). Elute the DNA with 45 µl of ddH$_2$O in a microcentrifuge tube.

5). Add 2 µl of the DpnI restriction enzyme (6 U/µl, from Life Technology) and 5 µl of 10×DpnI reaction buffer to each purified PCR product. Mix each reaction thoroughly and incubate them at 37° C. for 2 hours to digest the methylated and nonmutated parental DNA template.

6). Heat at 65° C. for 15 minutes to inactivate the DpnI restriction enzyme.

7). The circular, nicked and double-stranded DNA (dsDNA) is separated from other non-specifically amplified DNA by electrophoresis through a 0.8% agarose gel (from Boehringer Mannheim).

8). The DNA with the correct size is excised from the agarose gel and extracted from the gel slide using QIAquick Gel Extraction Kit (from QIAGEN). Elute the DNA with 40 µl of ddH$_2$O.

9). Transform 100 µl of competent *E. coli* BL21-DE-3 cells with 4 µl of DNA and select the colonies harboring the mutated pRSET-GFP plasmid (Heim, R. et al., 1995, Nature, 373: 663–664) on LB agar culture plates containing 100 µg/ml ampicillin (Sigma, St. Louis, Mo., USA).

Prepare Bacterial Cell Extracts Containing the Mutated GFP

1). A single green fluorescent colony was inoculated into 3–5 ml of LB medium containing ampicillin (100–200 µg/ml) in the morning. Cells were grown at 37° C. with shaking at 200 rpm/min until OD$_{600}$=0.7–0.9.

2). 0.4 mM IPTG (Promega, Madison, Wis., USA) was added into the cell culture to induce GFP expression at room temperature overnight. In addition, 200 µg/ml ampicillin was added to the cell culture to prevent plasmid loss during this long period of induction.

3). Cells were collected by centrifugation at 4,800 rpm for 5–10 minutes and washed once with 15 ml of cold PBS.

Cell pellets were resuspended in 0.3 ml of caspase assay buffer D containing 20 mM HEPES (from Life Technologies), 10 mM KCl (from Sigma), 5 mM DTT (from Boehringer Mannheim), 1 mM EDTA (from Sigma) and 0.1% CHAPS (Merck, Darmstadt, Germany), pH 7.2.

4). Cells were partially lysed by freezing in a dry ice/ethanol bath and thawing in a cold water bath. This process was repeated three times.

5). Cells were further lysed by sonication on ice for at least three times at 1 minute bursts/1 minute cooling at the maximum strength of the sonicator (Labsonic U).

6). Soluble proteins were separated from cell debris by centrifugation at 14,000 rpm for 10 minutes at 4° C. The clear supernatant was transferred into a microcentrifuge tube and stores at −20° C.

Characterization of GFP Mutants by Caspase-3 Assay, Fluorescence Measurement and Western Blot Analysis 10 µl of cell lysate prepared from each GFP mutant was mixed completely with 2.5 µl of active caspase-3 (20 ng/µl) (PharMingen, San Diego, Calif., USA) and 37.5 µl of the caspase assay buffer D. The reaction was carried out at 37° C. for 2 hours.

Each reaction mixture was then transferred into each well of a 96 well plate. The fluorescence intensity was measured using a fluorescence plate reader, CytoFluorII (Bioresearch, USA) with an excitation wavelength range of 468–492 nm and an emission wavelength range of 510–540 nm.

To perform Western blot analysis, 20 µl of the reaction mixture was mixed with 6 µl of 4×SDS page sample buffer containing 200 mM Tris-HCl, pH 6.8, 40% glycerol, 0.4% bromophenol blue (all from Sigma), 8% SDS (Riedel-de Haën), and 10% β-Mercaptoethanol (Fisher Scientific, Fair Lawn, N.J., USA). Protein samples were boiled for 5 minutes and subjected to SDS-PAGE on 12% or 15% gels. Proteins were subsequently electrotransferred onto a Hybond ECL nitrocellulose membrane (Amersham Life Science Ltd., Little Chalfont, Buckinghamshire, England). Protein blot was blocked with 5% non-fat dry milk and probed with polyclonal anti-GFP antibody at dilution of 1:5,000 (Molecular Probes Inc., Eugene, Oreg., USA) for 1–2 hours at room temperature. The membrane was washed 3–4 times for 5 minutes in TBS with 0.2% Tween-20 (from Sigma). The immunoblot was then probed with horseradish peroxidase-conjugated secondary goat anti-rabbit IgG antibody at dilution of 1:5,000 (Bio-Red, Hercules, Calif., USA). Finally, the proteins were detected using the ECL (R™) western blotting analysis system (from Amersham).

Generation of MD9 Mutant

A mammalian version of the EGFP mutant was generated usin the plasmid DNA of EGFP—C3 (Clontech, Palo Alto, Calif.) as a template in the mutagenesis experiments. The construct was prepared by following the procedures described above in the Materials and methods section under the heading "Generation of D9 mutant" from step 1 to step 9.

Generating stable mammalian cell lines expressing GFP-DEVD recombinant protein Using a stable transfection technique (below), the gene encoding GFP-DEVD (Table 2, MD9) is permanently integrated into the chromosomes of the target cells. In such a way, stable cell lines are generated that can automatically produce this intra-GFP probe. Such cell lines can then be used for the in vivo assay of apoptosis. These cell lines are particularly useful for rapid screening of drugs or for toxicity testing. The detailed procedure for generating such stable cell lines is described below:

(1) The plasmid DNA of EGFP mutants (see Table 2) containing an engineered caspase-3 cleavage site (SEQ ID NO: 4) was linearized by restriction digestion with EcoRI (Boehringer Mannheim). The position of the cleavage is within the multiple-cloning site region of the vector.

(2) 2–4 µg linear plasmid DNA was introduced into $5×10^5$ attached mammalian cells (e.g., HeLa) by electroporation.

(3) Cells were seeded into a 60-mm culture dish, and incubated at 37° C. with 5% $CO_2$ for 24–48 hours to allow the EGFP-DEVD mutant to be expressed.

(4) The efficiency of electroporation was determined by visualizing and counting the percentage of fluorescence positive GFP-DEVD cells under a fluorescence microscope.

(5) The cells were trypsinized and plated at dilution of 1:25 to 1:40 in the presence of 0.3–1.0 mg/ml antibiotic G418 (from Life Technologies). The concentration of G418 was determined by performing a kill curve with each particular cell line at a defined cell density.

(6) The selection medium was changed every 3 days for 14–20 days. Individual colonies exhibiting green fluorescence under a dissecting GFP microscope (Leica MZ12) were selected and expended into clonal cell lines.

(7) Genomic DNA from cells of the selected stable cell line was isolated and analyzed by Southern blot analysis to confirm the success of chromosomal integration of the GFP-DEVD gene.

Results a. We have generated mutated GFPs (above) with an insertion of a sensor sequence. These mutated GFP can retain the endogenous fluorescent properties.

The expression of the green fluorescent protein from each bacterial colony was examined under a fluorescent microscope (Leica MZ12) with excitation and emission filters for GFP. Green fluorescent signal was observed from various of the GFP mutants (Tables 1 and 2). The fluorescent intensity of some of the mutated GFP-DEVD was weaker than that of the wild-type GFP, but can still be detected clearly (FIG. 1).

b. These mutated GFP can be cleaved by caspase-3 as evident from Western blot assays.

Figure 2:
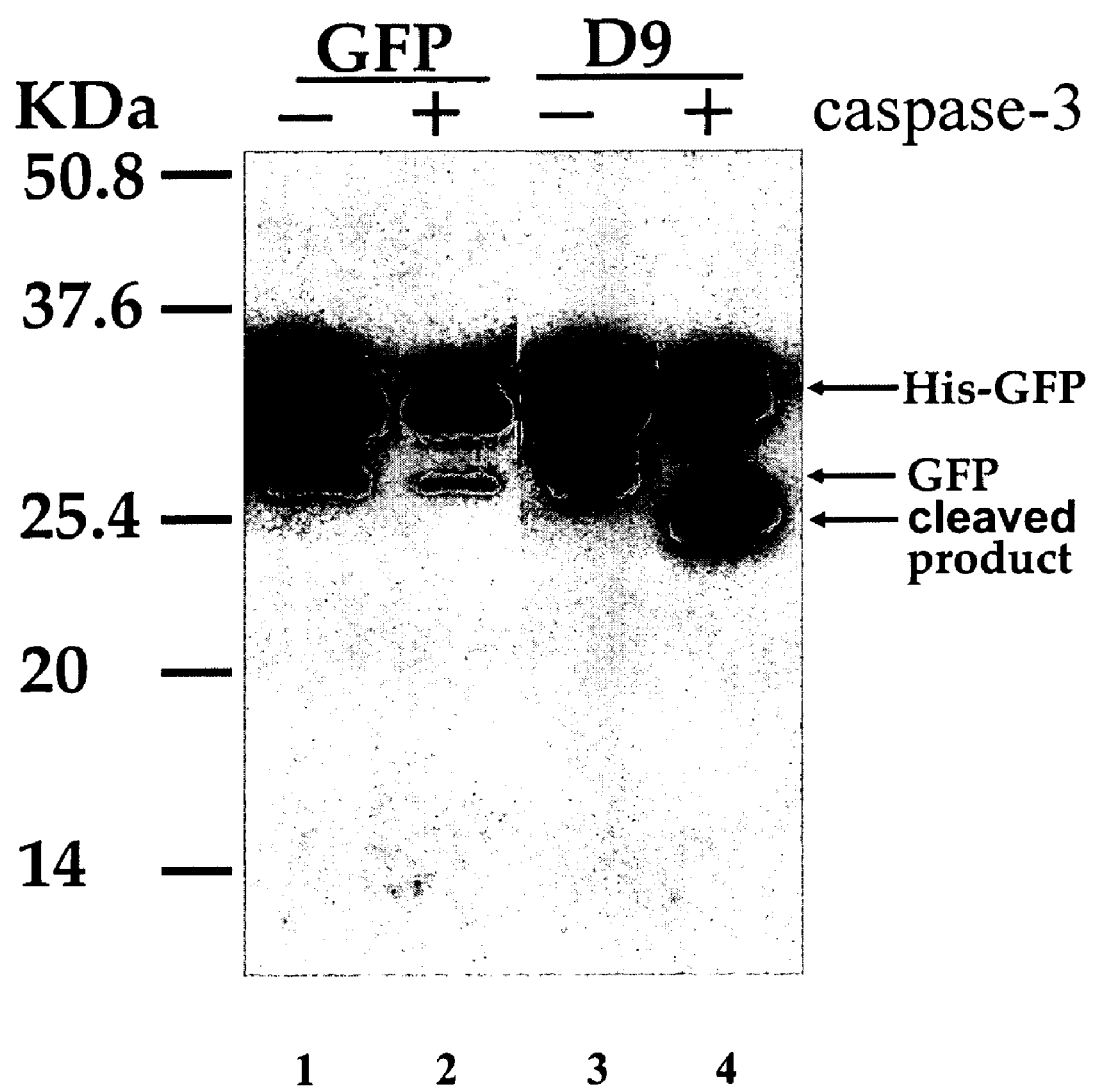
FIG. 2 shows Western blot analysis of caspase-3 cleavage using an anti-GFP antibody. Cell extracts of wild-type GFP clone (lanes 1 and 2) and GFP-DEVD mutant (clone D9) (lanes 3 and 4) were treated with (+) or without (−) caspase-3. Only the D9 mutant was cleaved by the caspase-3 treatment. The protein band with a smaller molecular weight seen in lane 4 represents the major cleavage fragment of GFP.

We then performed caspase assay on GFP mutants of D4, D7, D8, and D9 to determine which mutant can be cleaved by caspase-3. The cell extracts from each mutant were incubated with purified caspase-3 (PharMingen) at 37° C. for 2 hours, and then analyzed by Western blot assay using an anti-GFP polyclonal antibody (Clontech). The results are shown in FIG. 2. The GFP antibody interacted specifically with two bands with molecular weight corresponding to the poly-histidine tagged GFP and its degradation product from cells transfected with either GFP or mutant D9 (lanes 1 and 3). No proteins at the same molecular weights were detected by the GFP antibody from control cells expressing only the pRSET vector (data not shown). These results showed that the GFP antibody can detect both the wild type and the mutated GFP protein. When caspase-3 was added to the cell extract, the protein band of untagged GFP-DEVD disappeared while a new protein band representing the cleaved product emerged (lane 4), indicating that the mutant GFP was indeed cleaved by caspase-3. On the other hand, no cleavage occurred for the wild type GFP in the presence of caspase-3 (lane 2). Results of this in vitro assay clearly showed that the substration site (DEVD) inserted in the D9 mutant could be recognized and cleaved by the caspase-3. Similar Western blot analysis of cell extracts containing GFP mutants D4, D7 and D8 showed that those mutant proteins could also be cleaved by the caspase-3 (Tables 1 and 2).

c. When the mutated GFP was expressed in cultured mammalian cells, its fluorescent intensity was shown to decrease when cells entered apoptosis.

Figure 3:
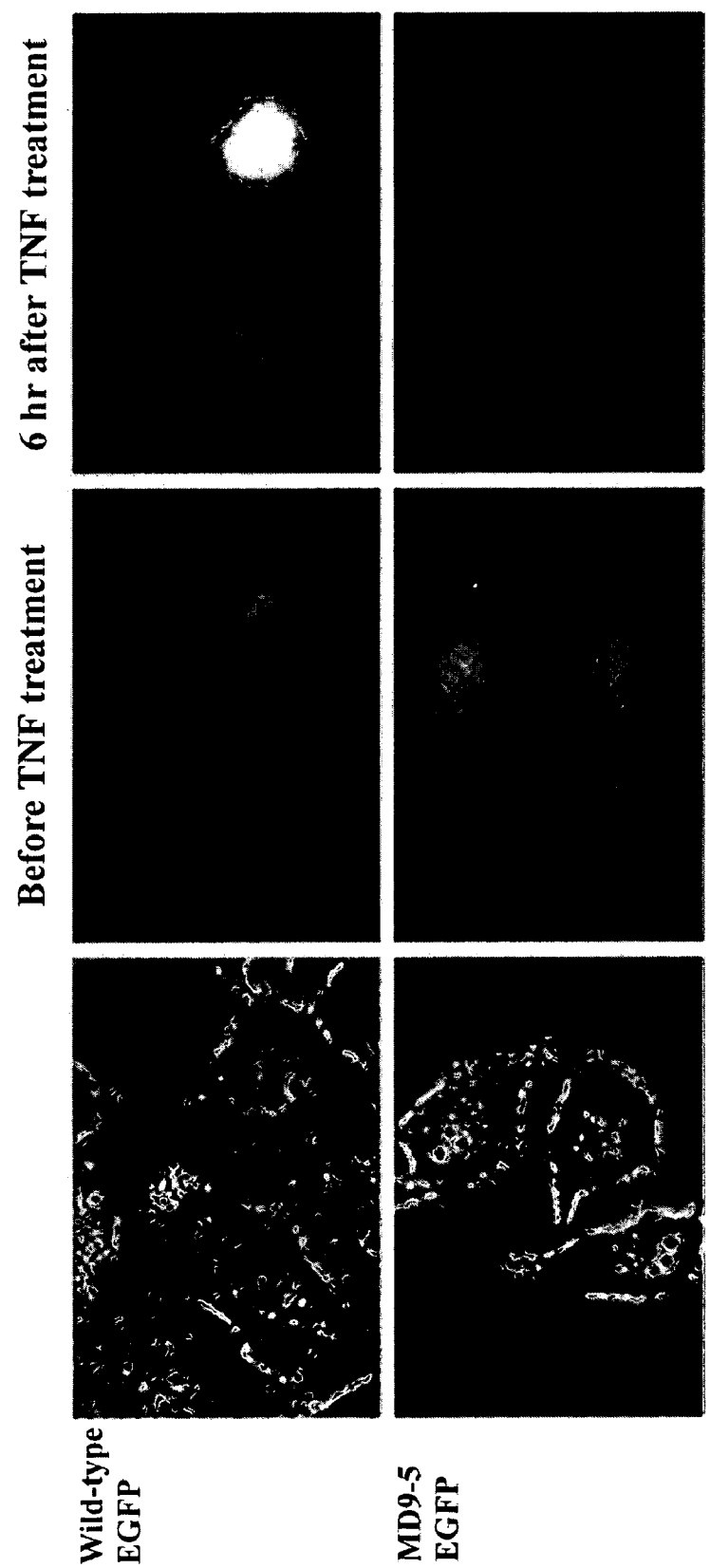
FIG. 3 shows phase contrast and fluorescent images showing the change of fluorescent intensity in HeLa cells transfected with wild-type GFP and mutant GFP (MD9) before and after the induction of apoptosis by TNFα treatment.
Figure 4:
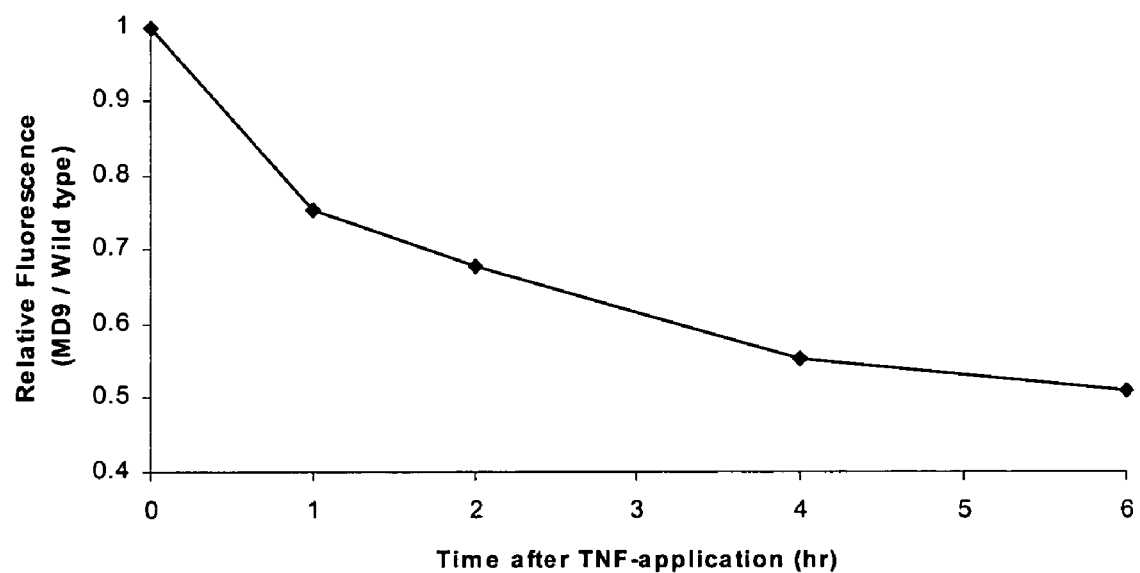
FIG. 4 shows relative fluorescence intensity of mutant GFP (MD9) in comparison to the wild-type GFP, measured as a function of time after HeLa cells were induced to enter apoptosis by a TNF treatment. Data is the average of four cells.
Figure 5:
FIG. 5 shows the principle of design of the intra-GFP probes of the present invention. A short peptide containing the substrate sequence of the caspase (referred to as "sensor") is inserted into the intra-molecular region of the GFP molecule. When caspase is activated, it cleaves the sensor and destroys the fluorescence properties of the GFP.
Figure 6:
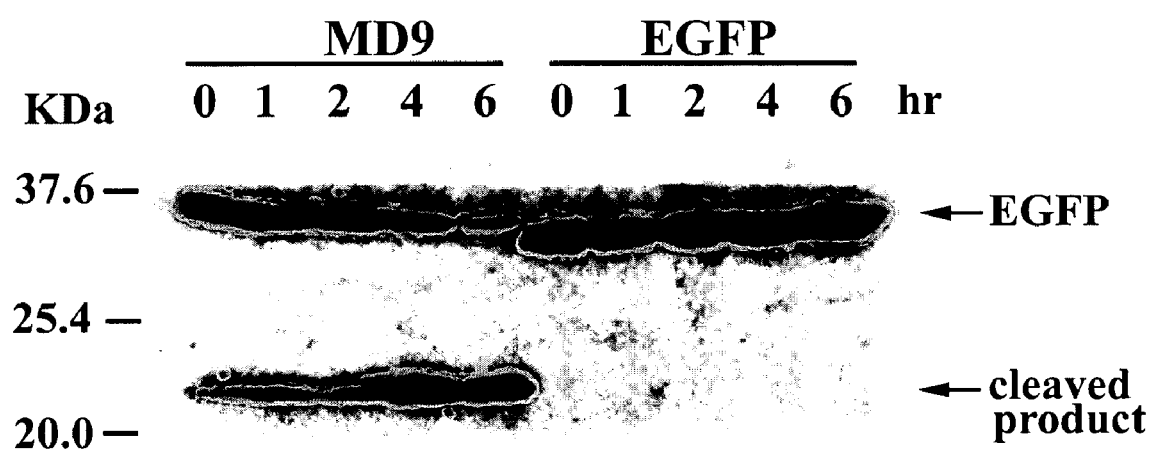
FIG. 6 shows Western blot analysis of MD9 mutant during TNF induced apoptosis. HeLa cells expressing either enhanced GFP (EGFP) or a mammalian version of D9 mutant (MD9) were treated with 5 ng/ml TNFa and 5 µg/ml of cycloheximide for 0, 1, 2, 4 and 6 hours. Cell extracts were analysed by Western blot. It is evident that only the MD9 mutant protein (but not EGFP) was cleaved during apoptosis.
Figure 7:
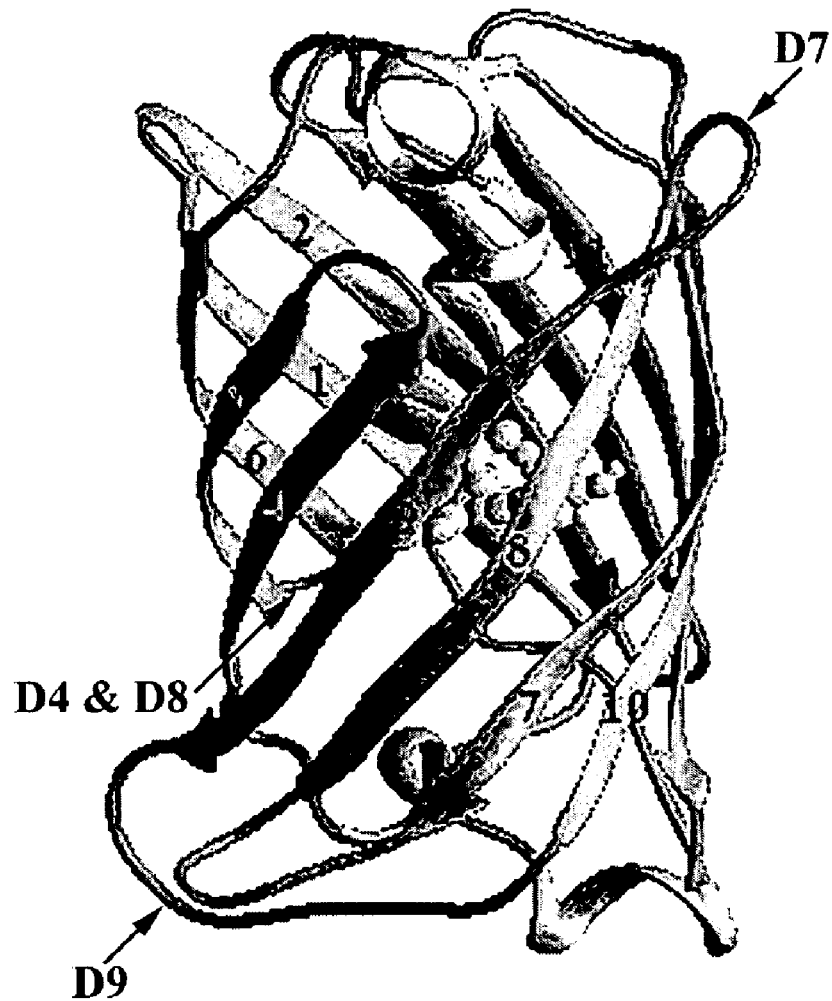
FIG. 7 shows the locations of mutation sites in GFP as shown in its 3-D structure. The mutation sites of D4, D7, D8 and D9 are all in the loop regions between different beta sheets. More specifically, mutant sites D4 and D8 are between the beta sheets No. 5 and No. 6. The site for mutant D7 is between beta sheets No. 8 and No. 9, and the site for D9 mutant is between beta sheets No. 9 and No. 10. The 3-D structure of GFP is based on the paper of Yang F., et al., 1996, Nature Biotechnology, 14:1246–1251.

To demonstrate that this newly developed mutant GFP probe can indeed be used in an in vivo assay of apoptosis, we have introduced plasmid DNA of both wild-type GFP (pEGFP—C3; SEQ ID NO: 32) and mutant GFP (MD9, the mammalian version of D9) into HeLa cells by electropration. The cells were seeded to a 35 mm-petri dish with a glass coverslip attached to the bottom, and cultured in a humidified $CO_2$ incubator at 37° C. At 30 hours after electroporation, the petri dish was transferred to a micro-incubation chamber (37° C.) and mounted onto the stage of an epi-fluorescence microscope. TNFα (5 ng/ml), together with cycloheximide (5 μg/ml), was applied to the cells to induce apoptosis. Fluorescent images of the cells expressing the fluorescent protein were recorded both before and after the induction of apoptosis. The fluorescent intensity inside the cells was measured using a computer-controlled imaging system (Li, C. J. et al., J. Cell Science, 112(10): 1567–1577). We found that the fluorescent intensity of cells transfected with mutant GFP (MD9) decreased significantly when cells entered apoptosis (FIG. 3). The relative fluorescence intensity of mutant GFP in comparison to wild type GFP was found to reduce by about 50% six hours after the TNFα treatment (FIG. 4). These results indicated that the fluorescent intensity of the mutant GFP, which has an insertion of caspase substrate (SEQ ID NO: 4) was indeed responsive to the activation of caspase-3 during apoptosis.

d. Western blot analysis of MD9 cleavage in TNF-induced apoptosis of HeLa cells

The plasmid DNA of MD9 and EGFP—C3 were transfected into HeLa cells, respectively, by electroporation. The cells were then seeded to 60 mm petri dishes and cultured in $CO_2$ incubator. After 48 hours of transfection, TNF (5 ng/ml), together with cycloheximide (5 μg/ml), was applied to the medium to induce apoptosis in these transfected cells. The samples were collected at 0, 1, 2, 4 and 6 hours after TNF-application, respectively, to perform Western blot analysis. When harvesting the cells, a plastic policeman was used to scrape the monolayer from the plate of the dish. The scraped cells were then transferred to a 15 ml centrifuge tube, together with the culture medium. The samples were centrifuged at 1500 rpm for 2 minutes. The pellet was washed with PBS once. Then 50 μl 1% SDS (in 10 mM Tris-HCl, pH 7.4) was applied to the pellet to lyse the cells. The cell lysate was centrifuged at 14,000×g for 3 minutes at 4° C. Then the supernatant was used to conduct Western blot analysis against the rabbit polyclonal antibody of anti-GFP (1:1000) from Molecular Probes, Inc. The result showed that the mutant GFP protein could be cleaved by activated caspase-3 in a time-dependent manner during the process of apoptosis. It can be seen from the figure that more than 50% of the mutant protein had been cleaved into smaller fragments after 4 hours of TNF-treatment. No cleavage had been seen in wild-type GFP during the process of apoptosis.

Example 2

To specifically determine protease (e.g. caspases) activity in sample cells of Example 1, the sample cells have their emission and/or excitation spectra determined. This is then compared to the same emission/excitation spectra determined for cells of Example 1 having a known protease activity, and the results then correlated to determine protease activity in the sample cells.

Example 3

To determine a change in protease (e.g. caspase) activity, the fluorescent intensity of sample cells is determined at a first timepoint using an imaging device. At a second timepoint the same fluorescent image is determined for the same cells. The results at the first and second timepoints are then compared and correlated to determine any change in protease activity.

To determine the rate of change of protease activity, at least one more timepoint must be added. Results can be standardised by comparing them to similarly obtained results for or cells having a known protease activity.

Example 4

To determine the effect of a compound or substance/composition on the activity of a protease in a cell or cells of Example 1, the method of Example 3 is employed but with the compound being administered to the cell between the first and second timepoints, the final correlation determining the effect of the compound upon the cell.

The method can be supplemented by comparison to similarly obtained results for a cell or cells having a known protease activity.

Example 5

To determine the effect of a compound or substance or composition on cells of Example 1, the method of Example 2 is employed but with the sample cells having first been treated with the compound, the final correlation determining the effect of the compound on the sample cells.

Example 6

Examples 4 and 5 concern the effect of one coumpound or substance/composition on the activity of a protease in a cell and on the cell. The effect of first and second compounds, the first compounds modify the apoptosis-inducing ability of the second compound, upon proteases and cells is determined by administering the first and second compounds at the same or different timepoints during the methods of Examples 4 and 5.

Example 7

The methods of Examples 2–6 need not be performed on cells and can instead be performed using mixtures of the necessary reagents (i.e. in a cell-free environment). As discussed above, GFP does not need any additional reagents such as ATP to fluoresce. Thus a mixture comprising a modified GFP of the present invention, chosen protease and the reagents and conditions necessary to allow fluorescence of the modified GFP are sufficient to allow an assay of protease activity. Other reagents and test compounds/compositions may also be included in the mixture to allow an analysis of their effect upon protease activity or fluorescence.

Example 7

An assay for determining the start of apoptosis comprises the method of Example 3, the correlation of results form the first and second timepoints determining any change in protease activity which indicates the onset of apoptosis.

TABLE 1

Mutants generated from GFP(S65T)

| Mutant Name | Mutation site(s) | Site(s) mutated to SEQ ID NO: | Fluorescent Intensity | Cleavage by caspase-3 |
|---|---|---|---|---|
| D1 | V22 | 14 | No | Not determined |
| D2 | G33–G35 | 15 | No | Not determined |
| D3 | D102–D103 | 16 | No | No |
| D4 | E115–D117 | 17 | 3+ | Partial |
| D5 | F130–E132 | 14 | No | Not determined |
| D6 | F130–E132 | 18 | + | No |
| D7 | E172 | 15 | 3+ | Partial |
| D8 | D117–T118 | 19 | 2+ | Partial |
| D9 | D190–G191 | 30 | 3+ | Partial |
| E2 | T118 | 20 | 2.5+ | Partial |
| E3-1 | G134 | 21 | 2+ | Partial |
| E3-5 | G134 | 22 | 2+ | Partial |
| E3-9 | G134 | 23 | 2+ | Partial |
| E3-12 | G134 | 24 | No | Partial |
| E4-a | V193 | 25 | 3+ | Partial |
| E4-g | V193 | 26 | 3+ | Partial |
| E4-j | V193 | 27 | 3+ | Partial |
| E4-o | V193 | 28 | 2+ | Partial |
| E4-p | V193 | 29 | 2+ | Partial |

The mutation sites referred to in Tables 1 and 2 are replaced in whole by the referenced SEQ ID NO. Thus for mutant D1, amino acid V22 is replaced by SEQ ID NO: 14. Similarly in mutant D8, amino acids D117 and T118 are replaced by by SEQ ID NO: 19. The fluorescent intensity of each clone detailed in Tables 1 and 2 was normalized against the fluorescence of positive controls of GFP(S65T) whose intensity was rated as 5+.

TABLE 2

Mutants generated from a mammalian version of GFP (EGFP)

| Mutant Name | Mutation site(s) | Site(s) mutated to SEQ ID NO: | Fluorescent Intensity | Cleavage by caspase-3 |
|---|---|---|---|---|
| β6 | F131–D134 | 31 | No | Not determined |
| β9 | G192–V194 | 14 | No | Not determined |
| β10 | P212–E214 | 14 | 3+ | No |
| MD9 | D191–G192 | 30 | 3+ | Partial |

TABLE 3

Caspases and their cleavage sites

| Protease | Alternative names | Recognition/ cleavage sequence (SEQ ID NO:) | Protein substrate |
|---|---|---|---|
| caspase-1 | ICE | 7 | Pro-IL-1β |
| caspase-2 | ICH-1/Nedd2 | 8 | PARP |
| caspase-3 | CPP32/Yama/ apopain | 4 | PARP, DNA-PK, SREBP1,2, rho-GDI |
| caspase-4 | TX/ICH-2/ ICErel-II | 9/10 | |
| caspase-5 | TY/ICErel-III | 9/10 | |
| caspase-6 | Mch2 | 11 | Lamin A |
| caspase-7 | Mch3/ ICE-LAP3/ CMH-1 | 4 | PARP, pro-caspase 6, SREBP1,2 |
| caspase-8 | MACH/FLICE/ Mch5 | 12 | PARP |
| caspase-9 | ICE-LAP6/ Mch6 | 13 | PARP |
| caspase-10 | FLICE2/Mch4 | | |
| caspase-11 | ICH-3 | | |
| caspase-12 | DRONC | | |
| caspase-13 | ERICE | | |
| caspase-14 | MICE | 4 | |

PARP: poly(ADP-ribose)polymerase
References: Cryns, V. and Yuan, J., 1998, Genes Dev., 11: 1551–1570; Cohen, G. M., 1997, Biochem. J., 326(pt1): 1–16; Negatta, S., 1997, Cell, 88: 355–365

References: Cryns, V. and Yuan, J., 1998, Genes Dev., 11: 1551–1570; Cohen, G. M., 1997, Biochem. J., 326(pt1): 1–16; Negatta, S., 1997, Cell, 88: 355–365

The invention claimed is:

1. A genetically engineered fluorescent protein which incorporates by insertion a protease cleavage site into said fluorescent protein, wherein said cleavage site is inserted between β-sheet pairs number 9 and 10, cleavage of said fluorescent protein at said cleavage site by a protease causes the alteration of at least one of an emission and an excitation spectra of said fluorescent protein, and wherein said fluorescent protein has the amino acid sequence of SEQ ID NO: 41.

2. The fluorescent protein according to claim 1, being a green fluorescent protein.

3. The fluorescent protein according to claim 1, wherein said cleavage site has the sequence SEQ ID NO: 4.

4. The fluorescent protein according to claim 1, said protease being a caspase.

5. The fluorescent protein according to claim 4, wherein said caspase is selected from the group consisting of caspase-3, caspase-6, caspase-7, caspase-8, and caspase-9.

* * * * *